(12) United States Patent
Mann et al.

(10) Patent No.: US 6,326,037 B1
(45) Date of Patent: Dec. 4, 2001

(54) MICROORGANISMS AND THEIR USE IN TREATING ANIMAL FEED AND SILAGE

(75) Inventors: Stephen Philip Mann, Cambridgeshire (GB); Sierk Fedde Spoelstra, Lelystad (NL)

(73) Assignees: Stichting Institut Voor (NL); Dierhouderij en Diergezondheid and Biotal Ltd. (GB)

( * ) Notice: Subject to any disclaimer, the term of this patent is extended or adjusted under 35 U.S.C. 154(b) by 0 days.

(21) Appl. No.: 09/637,459

(22) Filed: Aug. 11, 2000

Related U.S. Application Data

(63) Continuation of application No. 09/125,212, filed as application No. PCT/GB97/00433 on Feb. 17, 1997, now abandoned.
(60) Provisional application No. 60/016,988, filed on May 7, 1996.

(30) Foreign Application Priority Data

Feb. 15, 1996 (GB) .................................................. 9603168

(51) Int. Cl.$^7$ .................................................. A23B 7/155
(52) U.S. Cl. .................................................................. 426/52
(58) Field of Search ........................ 435/252.9; 426/623, 426/636, 44, 49, 52, 53, 61

(56) References Cited

U.S. PATENT DOCUMENTS

| | | | |
|---|---|---|---|
| 4,160,038 | 7/1979 | Groben et al. | 426/53 |
| 4,842,871 | 6/1989 | Hill | 426/44 |
| 5,747,020 | 5/1998 | Rutherford et al. | 424/93.45 |

FOREIGN PATENT DOCUMENTS

| | | |
|---|---|---|
| 0322569 | 4/1989 | (EP) . |
| 0408220 | 1/1991 | (EP) . |
| 0580236 | 1/1994 | (EP) . |
| 5084066 | 4/1993 | (JP) . |
| 1777772 | 11/1992 | (SU) . |
| 8002282 | 10/1980 | (WO) . |

OTHER PUBLICATIONS

Agricultural Research, Jun. 1995, p. 17, Cook, L.
Seale, D.R. and A.r. Henderson (1985) "Effect of inoculation with Homofermentative and Heterofermentative Lactic Acid Bacteria on Silage Fermentation", The Edinburgh School of Agriculture, U.K.
Dellaglio, F. et al. (1996) "DNA–DNA Homology, Physiological Characteristics and Distribution of Lactic Acid Bacteria isolated from Maize Silage," *Journal of Applied Bacteriology* 60(2):83–92.
Driehuis, F., et al., "Improving Aerobic Stability by Inoculation with *Lactobacillus buchnen*" Proceedings of the 11$^{th}$International Silage Conference, 106–107, Sep. 1996.
Muck, R. E. "A Lactic Acid Bacterial Strain to Improve Aerobic Stability of Silages," *Researc Summarines of the U.S. Dairy Forage Research Center*, 46–47, Oct. 1997.
Weinberg, Z.G. et al. "New Trends and Opportunities in the Development and Use of Inoculants for Silage,"FEMS Microbiology Reviews 19:53–68.

*Primary Examiner*—Keith Hendricks
(74) *Attorney, Agent, or Firm*—Saliwanchik, Lloyd & Saliwanchik

(57) ABSTRACT

The subject invention pertains to methods for treating silage which comprises adding to the silage a microorganism having the characteristic of *Lactobacillus buchneri*, NCIMB 40788, to produce a secondary metabolite as well as fatty acids normally produced in fermentation, and further comprising maintaining the silage closed for a period sufficient for the secondary metabolite to accumulate. This secondary metabolite has the ability to inhibit the growth of spoilage organisms including yeasts, molds and spore-forming bacteria.

40 Claims, No Drawings

MICROORGANISMS AND THEIR USE IN TREATING ANIMAL FEED AND SILAGE

CROSS-REFERENCE TO A RELATED APPLICATION

This application is a continuation of application Ser. No. 09/125,212, filed Mar. 22, 1999 now abandoned, which is a national stage application of international application No. PCT/GB97/00433, filed Feb. 17, 1997, which claims priority to provisional application Ser. No. 60/016,988, filed May 7,1996.

FIELD OF THE INVENTION

This invention relates to microorganisms and their use in treating animal feed and silage.

BACKGROUND OF THE INVENTION

The use of enzymes and organisms can improve or enhance the performance of animals and the value of the feed the animals receive. For example, WO-A-9210945 discloses such a combination for use in enhancing the value of prepared silage, and WO-A-9617525 relates to enhancement of animal performance using microorganisms. The efficacy of combining the use of enzymes together with organisms producing volatile fatty acids (VFA's) is also described. In this case, better preservation of the silage, better animal performance and a reduction in effluent production were demonstrated. WO-A-9503396 demonstrates that some advantages may accrue when a desired VFA profile is produced during the silage fermentation; it has also been found that this does not produce the desired reduction in heating, on opening the silage clamp.

The production of silage and the associated crop husbandry have over recent years developed to an extent that a number of different processes can be defined. These are: (i) the ensiling of young grass with particularly low dry matter, e.g. less than 25% (common in UK, Ireland and Scandinavia), (ii) the ensiling of higher dry matter, more mature grasses (UK), the ensiling of high dry matter but young grass achieved by wilting (Netherlands); and (iii) the ensiling of whole maize including stova and cob, usually at a dry matter concentration of about 35%, and whole crop cereals, e.g. wheat, at 45–50% dry matter.

Particularly in cases (ii) and (iii), one major problem occurs on a regular basis. This is the phenomenon known as aerobic spoilage. This phenomenon is not well understood. Although there are many differing opinions, the process of aerobic spoilage can be divided into phases. Thus, there is an initial phase in which yeasts and sometimes acetic acid bacteria start to respire the preserving organic acids. After an initial rise in pH, there is a secondary phase in which the activity of bacilli is apparent, and is associated with increasing temperature. A further phase includes activity of various microorganisms including fungi.

In those silages which contain a substantial content of dry matter, i.e. over 30%, the problem of spoilage is particularly acute. Spoilage is seen to a greater or lesser extent once a silage clamp is opened and exposed to air.

SUMMARY OF THE INVENTION

This invention is based at least in part on identifying the aerobic spoilage process as being closely related to heating in the clamp on exposure to the ingress of air. Subsequent examination of such silages showed high concentration of thermophilic Gram-positive organisms, yeasts and bacteria including bacilli and fungi. This apparently demonstrates the onset of a secondary fermentation, akin to that of composting (the primary fermentation being the ensiling process). In this fermentation stage, yeast and moulds predominate. It appears that, in order to prevent spoilage, three main categories of organisms that need to be killed or suppressed are spore-forming bacteria, yeasts and fungi. To eliminate only one category may lead to the proliferation of the remaining categories, so that spoilage is not prevented.

According to this invention, utility in the prevention of spoilage has been identified in materials that, at least in the first instance, inhibit microorganisms that initiate aerobic spoilage, notably yeasts and, at the surface of silage, fungi. An organism capable of doing this may also inhibit the development of other spoilage microorganisms, and may be identified by screening.

An organism of the species *Lactobacillus buchneri*, that meets this requirement has been deposited at the National Collection of Industrial and Marine Bacteria on 13th Feb. 1996. Its accession number is 40788.

As explained in more detail below, this organism has a surprising effect, different from and/or extending beyond that due to its ability to produce VFA's, such as acetic, propionic and lactic acids, that are normally produced in fermentation. The organism produces an antimicrobial substance or effect characterised by its ability to inhibit the growth of a variety of spoilage organisms, and which is stable at 80° C. but inactivated at 120° C. It is reasonable to assume that any such substance (which may possibly be proteinaceous) may be produced by other organisms. Any one of ordinary skill in the art, provided with the information in this specification, will be able to identify whether any given organism, other than that which has been deposited, produces the same substance.

The substance may be isolated and purified by methods known to those of ordinary skill in the art. As such, it may be used directly to treat animal feed or silage. In other words, it may not be necessary to use a microorganism as such in the method of this invention.

DESCRIPTION OF THE INVENTION

For the purpose of illustrating the invention, an organism has been identified that is capable of producing an approximately normal silage fermentation together with a substance that can inhibit the other organisms thought to be associated with aerobic spoilage. Furthermore, when inoculated on whole crop wheat, maize and grass silage, this organism produces a silage that is well preserved and in which the onset of secondary fermentation associated with aerobic spoilage and heating is reduced or eliminated. The organism thus appears to be able to produce the inhibitory substance under the conditions of fermentation found in silages. A VFA profile as usually obtained in well-fermented silages (with or without the use of inoculants including *Lactobacillus plantarum*) has been proven to be insufficient to prevent the occurrence of aerobic spoilage.

It appears that the inhibitory substance may be a secondary metabolite. Therefore, its full effect may not be seen if, when used in silage, that silage is opened too soon. The silage is preferably kept closed for at least 30 days, and more preferably for a longer period, e.g. at least 45 days. The optimum period will depend, e.g. inter alia, on the size of the silage mass, and the nature of the ensiled material.

Materials that are suitable for ensiling, in this invention are any susceptible to aerobic spoilage. The material will usually contain at least 25% by weight dry matter. Such materials include rye or traditional grass, maize, Lucerne, wilted grass, wheat, barley or other whole crop cereal. The silage may be in bales (a form particularly susceptible to aerobic spoilage). Alternatively, the invention may be used with any susceptible animal feed, whether solid or liquid, e.g. for pigs, poultry or ruminants.

The activity associated with this invention may be found in other strains of *L. buchneri*, in other species of *Lactobacillus*, e.g. *L. kefir, L. parakefir* and *L. parabuchneri*, and possibly also in other genera. This can be established by routine experimentation, on the basis of the information herein.

The activity is valuable in inhibiting the growth of various spoilage organisms. Examples of such organisms are Listeria organisms, Bacillus spp., *Guillermondella* selenospora, Trichoderma longibrachiatum, Aspergillus niger, Monascus, *Pennicillium roquefortii*, Fusarium spp., and enteric bacteria such as Salmonella.

Selected organisms were grown in liquid culture and the fermentation medium was separated from the cells. This medium was then used in trials to ascertain if there was present an inhibitory substance that could provide the desired effect, i.e. of heat-stable silage.

Experiments were conducted with three typical organisms that epitomise the spoilage process, i.e. a Bacillus, a yeast and a fungus. Several combinations of the VFA's lactate, acetate, propanoate were also tested. Only the extract from a small number of selected organisms produced the desired inhibitory result. This demonstrated that bacteria were capable of producing one or more substances inhibitory to the target organisms.

In order to demonstrate that such organisms could indeed prevent aerobic spoilage, further experiments were conducted. Organisms were cultured by conventional means and re-inoculated on to grass or whole crop wheat, in c. 10 kg batches, where the organism produced a fermentation not unlike that of a conventional ensiling fermentation, typical for the material ensiled. The nature of this fermentation is not fully understood, but the loss of dry matter (approx 4%) as gas, presumably $CO_2$, indicates that this may well be a partially heterofermentative fermentation. Silage prepared in this way proved to have a VFA profile approximating to that of a normal silage. There was no evidence that silages prepared by inoculating with this organism in combination with enzymes would give the desired results. However, silages prepared in this way were taken and placed in large plastic boxes, approximately 0.5 m =0.25 m by 0.1 m. The boxes were approximately half-filled. Thermocouples were placed in the silages to recorded the onset of the heating phase of the aerobic spoilage. Each box was placed on an open lab with excellent ventilation.

The results of one such experiment are given in Example 1, below. The results indicate an apparently normal silage fermentation, but in a remarkable demonstration of the effects of the antimicrobial activity of the organism, the treated silage was thermostable, maintaining ambient temperatures (20° C.) for a period of at least ten days. In control and other treatments, the temperature rose to more than 35° C.

EXPERIMENT 1

Whole crop wheat was treated with a formulation consisting of freeze-dried cells and enzymes. The formulation comprised 4.87% *L. buchneri* NCIMB 40788, 10.67% enzymes comprising β-glucanase, xylanase and galactomannanase, 80.09 % caster sugar, 3.13% Drimalan green BGE and 1.25% Sipernat 50S. These figures are based on a freeze-dried cell concentration of $3=10^{11}$/g *L. buchneri*. This pale green, free-flowing powder formulation was used by dissolving 150 g in 100 l water, to treat 25 tonnes of forage, by spraying at an application rate of 4 litres per tonne. The viable count was $5 \times 10^4$ cfu/g whole crop wheat.

As the control, a conventional silage inoculant containing *Pediococcus pentosaceus* (NCIMB 12455) and *Lactobacillus plantarum* (NCIMB 12422) was used. This is representative of organisms conventionally used in silage treatment, and is described below as the "normal inoculant".

The formulation was enclosed in fermentation barrels with vents to allow the normal fermentation process. The contents were examined after 130 days' analysis and aerobic stability tests were then carried out.

| | Fermentation profiles | | | | |
|---|---|---|---|---|---|
| Treatment | DM (%) | pH | CP (%) | ME (MJ/Kg) | $NH_3$ (%) |
| Untreated | 49.6 | 4.1 | 12 | 10.6 | 0.11 |
| Normal Inoculant | 50.3 | 3.9 | 10 | 10.7 | 0.12 |
| Test organism | 51.0 | 4.0 | 10.4 | 10.1 | 0.11 |

| | Product profiles | | | |
|---|---|---|---|---|
| | lactate | acetate | propionate | ethanol |
| Untreated | 41 | 1 | 0 | 6 |
| Normal inoculant | 45 | 5 | 0 | 3 |
| Test organism | 35 | 4 | 0 | 6 |

| | Temp. development (° C.) | | | | | |
|---|---|---|---|---|---|---|
| Treatment (hours) | 0 | 50 | 100 | 150 | 200 | 250 |
| Untreated | 17 | 17 | 17 | 35 | 34 | 25 |
| Normal inoculant | 17 | 17 | 17 | 25 | 27 | 36 |
| Test organism | 17 | 17 | 17 | 17 | 17.5 | 18 |

These results, albeit on a small scale, demonstrate that the mechanism is not dependent on VFA profiles or VFA concentration.

EXPERIMENT 2

Bigbale grass silage was prepared, and treated with a similar formulation as in Example 1, additionally comprising amylase, to provide $1 \times 10^5$ cfu/g grass, at an application rate of $1 \times 10^5$ g forage. Control silages and silages treated with the *L. buchneri* strain were examined and analysed after periods of 28, 63, and 113 days of ensiling. The composition of the bigbale silage was as follows:

| | Day 28 | | Day 63 | | Day 113 | |
|---|---|---|---|---|---|---|
| Dry matter (g/kg) | 335 | 373 | 361 | 367 | 328 | 337 |
| pH | 4.48 | 4.57 | 4.42 | 4.49 | 4.40 | 4.47 |
| Lactate (g/kg DM) | 54 | 54 | 66 | 59 | 78 | 71 |
| Acetate | 11 | 13 | 15 | 19 | 21 | 27 |
| Propionate | 0.7 | 0.7 | 0.6 | 0.7 | 0.8 | 1.0 |
| Ethanol | 8 | 8 | 7 | 8 | 9 | 10 |
| $NH_3$—N (% N) | 9 | 8 | 11 | 10 | 12 | 12 |
| Aerobic stability (h) | 138 | 178 | 187 | 222 | 150 | >189 |

The results of Experiment 2 again demonstrate that the differences between the control and the invention are not simply due to the production of a particular VFA profile. Moreover, there is an indication that the stability of the silage on exposure to air increases with time. This indicates a specific mode of action of the organism *L. buchneri* and others with similar activities.

From the above results, it would appear that the mechanism of action is the production of at least one antimicrobial substance by the selected micro-organisms during the fermentation process. In order to characterise the nature of the antimicrobial substance, experiments were undertaken which demonstrated that the substance produced in the supernatant of fermantation broth of the selected organism did inhibit a wide range of micro-organisms. It was stable to heat treatment for 10 min at 80° C., but was inactivated by heat for 10 min at 120° C. the VFA's also present in the fermentation broth appeared to have negligible or no effects on the growth of selected spoilage organisms

EXPERIMENT 3

The mechanism of action was further demonstrated by a series of experiments in which culture supernatants were prepared after 24 and 48 hours' incubation in flask cultures. These supernatants were examined on specific organisms known to be active in the aerobic spoilage of fermentations such as those which occur in silage.

In this Experiment, attention was focused on the organisms falling into the yeast and mould categories. The effects of the supernatant were examined on the moulds, *Fusarium oxysporum* (IMI 236441), *Mucor racemosus* (IMI 103730), *Aspergillus niger* (IMI 096215), *Caldosporum hebarum* (IMI 096220), *Penicillum expansum* (IMI 315902) and *Trichoderma harzanium* (IMI 275950), and the yeasts *Candida krusei* (ATCC 62403), *Guilliermondella selenospora* (ATCC 10629), *Debraryomyces hansenii* (ATCC 9364) and *Pichia subpellicosa* (ATCC 16766 ).

In each case, inhibition of the growth of the target organisms was demonstrated. In addition, those supernatants that were prepared from the broth following 48 hours' incubation generally showed the greater inhibitory activity than those incubated for 24 hours. This suggests that the antimicrobial effect is produced at a late stage in the calls' growth cycle, or that it accumulates with time, or that both these possibilities occur. The antimicrobial effect may thus accumulate at an increasing rate, with every generation. It is therefore desirable that, in the field, the fermentation should take place in an optimal manner and that the fermentation should continue for such a time as shall provide for the maximal accumulation of the antimicrobial effect. The time taken for production of the antimicrobial effect in the field, will vary with the conditions and with the nature of the forage that is being ensiled.

EXPERIMENT 4

To demonstrate the effect of time on the prevention of aerobic spoilage, grass silage was prepared as in Experiment 1. The aerobic stability was then determined. At 7 days, the stability of the silage was poor with heating occurring in line with the control. At 100 days, stability was assured.

We claim:

1. A method for treating silage to prevent or reduce aerobic spoilage which comprises adding to said silage an inoculant composition consisting essentially of *Lactobacillus buchneri* and maintaining the silage closed for a period of at least 30 days subsequent to the addition of said inoculant; wherein said *L. buchneri* prevents the temperature of whole crop wheat silage, dry matter content 45 %, from rising from 17° C. by more than 4° C. over 200 hours.

2. The method according to claim 1, wherein the silage is of traditional grass.

3. The method according to claim 1, wherein the silage is of maize.

4. The method according to claim 1, wherein the silage is of Lucerne.

5. The method according to claim 1, wherein the silage is of wilted grass.

6. The method according to claim 1, wherein the silage is of whole crop cereal.

7. The method according to claim 1, wherein said *L. bucheri* is *Lactobacillus buchneri*, NCIMB 40788.

8. The method according to claim 2, wherein the traditional grass is rye grass.

9. The method according to claim 6, wherein the whole crop cereal is wheat or barley.

10. A method for treating silage to prevent or reduce aerobic spoilage, which comprises adding to said silage an inoculant composition consisting essentially of *Lactobacillus buchneri* and maintaining the silage closed for a period of at lest 30 days subsequent to the addition of said inoculate, wherein said treated silage is essentially thermostable maintaining ambient temperatures for a period of at least ten days.

11. The method according to claim 10, wherein the silage is of traditional grass.

12. The method according to claim 10, wherein the silage is of maize.

13. The method according to claim 10, wherein the silage is of Lucerne.

14. The method according to claim 10, wherein the silage is of wilted grass.

15. The method according to claim 10, wherein the silage is of whole crop cereal.

16. The method according to claim 10, wherein said *L. buchneri* has the ability to prevent the temperature of whole crop wheat silage, dry matter content 45%, from rising from 17° C. by more than 4° C. over 200 hours.

17. The method according to claim 10, wherein said *L. buchneri* is *Lactobacillus buchneri*, NCIMB 40788.

18. The method according to claim 11, wherein the traditional grass is rye grass.

19. The method according to claim 15, wherein the whole crop cereal is wheat or barley.

20. The method, according to claim 10, wherein said silage has a dry matter content of over 30%.

21. A method for treating silage to prevent or reduce aerobic spoilage, which comprises adding to said silage an inoculant composition consisting essentilly of *Lactobacillus buchneri*, wherein said *Lactobacillus buchneri* composition prevents the temperature of whole crop wheat silage, dry matter content 45%, from rising from 17° C. by more than 4° C. over 200 hours.

22. The method according to claim 21, wherein the silage is of traditional grass.

23. The method according to claim 21, wherein the silage is maize.

24. The method according to claim 21, wherein the silaage is of Lucerne.

25. The method according to claim 21, wherein the silage is of wilted grass.

26. The method according to claim 21, wherein the silage is of whole crop cereal.

27. The method according to claim 21, wherein said *Lactobacillus bachneri* is *Lactobacillus buchneri*, NCIMB 40788.

28. The method according to claim 22, wherein the traditional grass is rye grass.

29. The method according to claim 26, wherein the whole crop cereal is wheat or barley.

30. A method for treating silage to prevent or reduce aerobic spoilage, which comprises adding to said silage an inoculant composition consisting esssentially of *Lactobacillus buchneri*, wherein said treated silage is essentially theremostable and maintains ambient temperatures for a period of at least ten days.

31. The method according to claim 30, wherein the silage is of traditional grass.

32. The method according to claim 30, wherein the silage is of maize.

33. The method according to claim 30, wherein the silage is of Lucerne.

34. The method according to claim 30, wherein the silage is of wilted grass.

35. The method according to claim 30, wherein the silage is of whole crop cereal.

36. The method according to claim 30, wherein said *L. buchneri* has the ability to prevent the temperature of whole crop wheat silage, dry matter content 45%, from rising from 17° C. by more than 4° C. over 200 hours.

37. The method according to claim 30, wherein said *L. buchneri* is *Lactobacillus buchneri*, NCIMB 40788.

38. The method according to claim 31, wherein the traditional grass is rye grass.

39. The method according to claim 35, wherein the whole crop cereal is wheat or barley.

40. The method according to claim 30, wherein said silage has a dry matter content of over 30%.

* * * * *

UNITED STATES PATENT AND TRADEMARK OFFICE
CERTIFICATE OF CORRECTION

PATENT NO. : 6,326,037 B1
DATED : December 4, 2001
INVENTOR(S) : Stephen Philip Mann and Sierk Fedde Spoelstra It is certified that error appears in the above-identified patent and that said Letters Patent is hereby corrected as shown below:

Column 6,
Line 19, "*buchneri*and" should read -- *buchneri* and --.
Line 20, "at lest" should read -- at least --; and "inoculate" should read -- inoculant --.
Line 56, "is maize" should read -- is of maize --.
Line 64, "*bachneri*" should read -- *buchneri* --.

Signed and Sealed this

Twenty-third Day of April, 2002

Attest:

*Attesting Officer*

JAMES E. ROGAN
*Director of the United States Patent and Trademark Office*